United States Patent
Roberts et al.

(10) Patent No.: US 6,872,223 B2
(45) Date of Patent: Mar. 29, 2005

(54) CONTROLLED DEPLOYMENT OF A MEDICAL DEVICE

(75) Inventors: George T. Roberts, Weston, MA (US); Kathleen L. Hess, Lynn, MA (US); Sepideh H. Nott, Fall River, MA (US); Michael S. H. Chu, Brookline, MA (US); Yem Chin, Burlington, MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 09/968,149

(22) Filed: Oct. 1, 2001

(65) Prior Publication Data

US 2002/0045914 A1 Apr. 18, 2002

Related U.S. Application Data

(63) Continuation of application No. 09/048,953, filed on Mar. 26, 1998, now Pat. No. 6,296,660, which is a continuation of application No. 08/471,380, filed on Jun. 6, 1995, now Pat. No. 5,908,448, which is a continuation of application No. 08/269,064, filed on Jun. 30, 1994, now Pat. No. 5,545,209, which is a continuation-in-part of application No. 08/130,020, filed on Sep. 30, 1993, now abandoned.

(51) Int. Cl.$^7$ ................................................. A61F 2/06
(52) U.S. Cl. ................................................. 623/1.11
(58) Field of Search .......................... 623/1.11, 1.12, 623/1.3, 1.15, 1.23; 606/194, 191–192; 604/101.01–101.03, 103.05, 103.06, 103.07–103.09, 103.11–104

(56) References Cited

U.S. PATENT DOCUMENTS

| | | | |
|---|---|---|---|
| 4,564,014 A | | 1/1986 | Fogarty |
| 4,990,155 A | * | 2/1991 | Wilkoff ...................... 606/191 |
| 5,116,318 A | * | 5/1992 | Hillstead ............... 604/103.14 |
| 5,123,917 A | * | 6/1992 | Lee ........................... 623/1.13 |
| 5,147,385 A | | 9/1992 | Beck |
| 5,366,473 A | | 11/1994 | Winston et al. |
| 5,409,495 A | * | 4/1995 | Osborn ...................... 623/1.11 |
| 5,522,882 A | * | 6/1996 | Gaterud et al. ............ 623/1.11 |
| 6,296,660 B1 | * | 10/2001 | Roberts et al. ........... 623/1.11 |

\* cited by examiner

*Primary Examiner*—Anhtuan T. Nguyen
*Assistant Examiner*—(Jackie) Tan-Uyen T. Ho
(74) *Attorney, Agent, or Firm*—Fish & Richardson P.C.

(57) ABSTRACT

A prosthesis delivery system having a balloon catheter with an inflatable balloon on its exterior. The balloon is inflatable by injection of fluid through a lumen in the catheter and the balloon is initially partially constrained against inflation by a constraint. A tubular prosthesis is disposed on the catheter over at least a portion of the balloon and a portion of the constraint. The tubular prosthesis has a contracted condition and an expanded condition. The tubular prosthesis is initially disposed on the catheter in the contracted condition. Further, a balloon catheter includes a constraint so that the balloon may be sequentially inflated for dilatation purposes such as in a valvuloplasty operation.

24 Claims, 18 Drawing Sheets

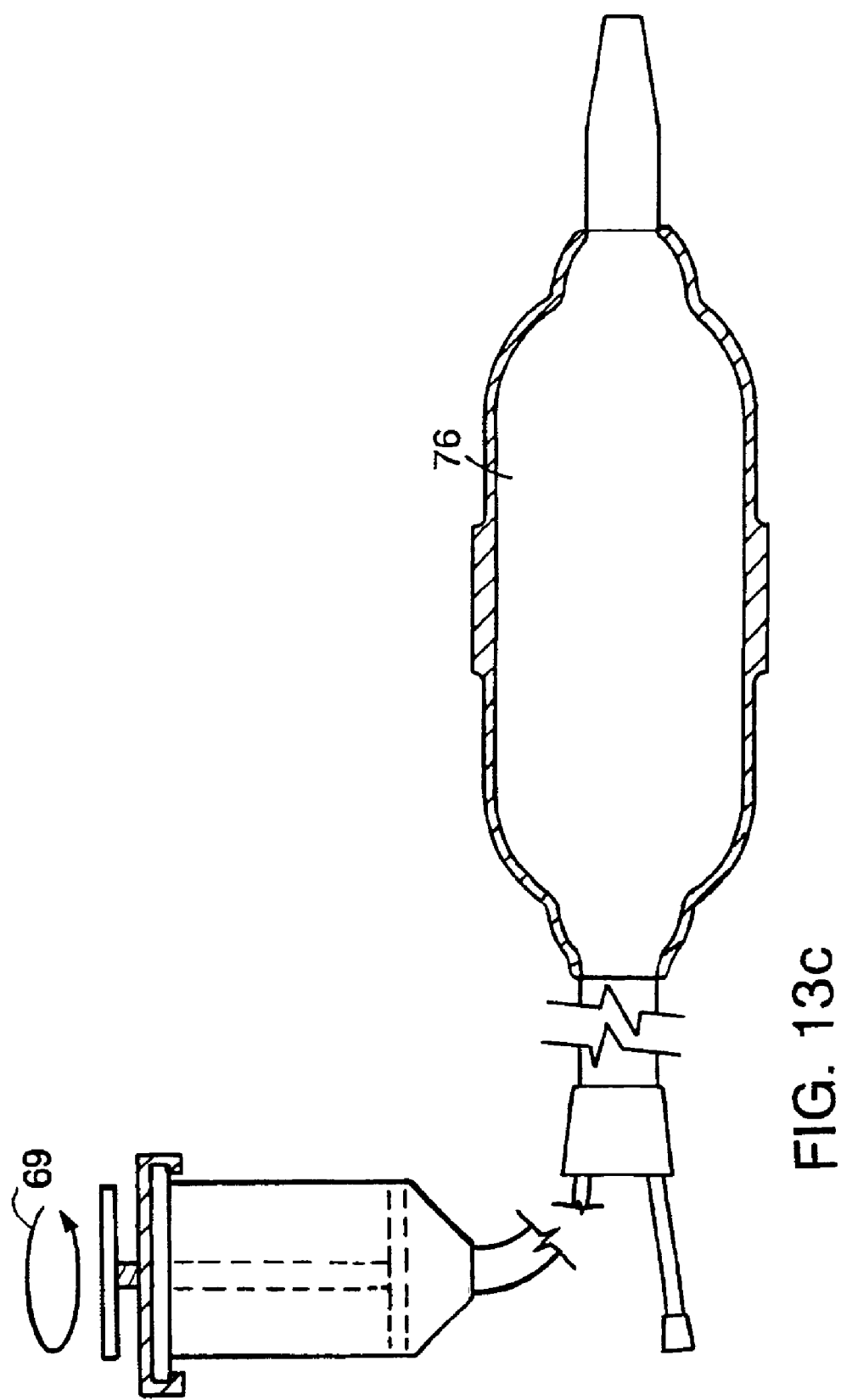

CONTROLLED DEPLOYMENT OF A MEDICAL DEVICE

CROSS-REFERENCE TO RELATED APPLICATION(S)

This application is a continuation of U.S. application Ser. No. 09/048,953, filed Mar. 26, 1998 now U.S. Pat. No. 6,296,660; which is a continuation of U.S. application Ser. No. 08/471,380, filed Jun. 6, 1995 now U.S. Pat. No. 5,908,448; which is a continuation of U.S. application Ser. No. 08/269,064, filed Jun. 30, 1994, now U.S. Pat. No. 5,545,209; which is a continuation-in-part of U.S. application Ser. No. 08/130,020, filed Sep. 30, 1993 now abandoned. The disclosure of the prior applications is considered part of (and incorporated by reference in) the disclosure of this application.

BACKGROUND OF THE INVENTION

This invention relates to controlled deployment of medical devices such as endoprostheses and balloons.

Prostheses are used in body lumens that have been occluded or weakened by disease. For example, to treat arterial stenoses, an endovascular stent is implanted to hold the lumen open and to prevent any flaps or dissections on the lumen wall from occluding the lumen. To treat aneurysms, a prosthesis in the form of a graft is attached to healthy portions of the lumen on either side of the aneurysm so that the body of the graft bridges the weakened area. The wall of these grafts is initially permeable, but through clotting action, becomes fluid impermeable. This reduces the pressure in the aneurysm and hence, the likelihood that it will rupture.

Prostheses are typically delivered into the body on a catheter in small diameter form and then expanded to engage the lumen at the desired site. They may be self-expanding, i.e., they expand from a small diameter to a larger diameter by their own elastic forces after removal of a restraint, or they may be expanded by radial force from within the prosthesis, provided, for example, by an inflatable balloon on the end of the catheter.

In a procedure known as valvuloplasty, a balloon is used to open a valve in the heart. In this case, the physician urges the catheter through the closed valve to position the balloon beyond it. A controlled inflation is then effected such that the distal end of the balloon inflates to a diameter larger than the valve. The catheter is then withdrawn proximally until the physician feels resistance caused by the inflated portion of the balloon engaging the inner walls of the valve. A proximal portion of the balloon is then inflated which centers the balloon about the valve. Finally, the central portion of the balloon is inflated to dilate the valve.

SUMMARY OF THE INVENTION

In a first aspect, the invention features a prosthesis delivery system. The system includes a balloon catheter having an inflatable balloon on its exterior. The balloon is inflatable by injection of fluid through a lumen in the catheter. The balloon is initially partially restrained against inflation by a constraint. A tubular prosthesis is disposed on the catheter over at least a portion of the balloon and a portion of the constraint. The tubular prosthesis has a contracted condition and an expanded condition. The tubular prosthesis is initially disposed on the catheter in the contracted condition.

Embodiments may include one or more of the following features. The balloon is only initially radially constrained. The constraint is an axially slidable sheath which surrounds and partially constrains the balloon from inflation. The sheath is designed to axially slide along a length of the balloon in response to a pressure in the balloon, such that the balloon may be progressively incrementally inflated. The slidable sheath is adapted to slide axially onto a shaft of the catheter so that the sheath may be retrieved from the patient. The constraint is an elastomeric band which surrounds and partially constrains the balloon from inflation. The elastomeric band is disposed over a significant length of the balloon. The elasticity of the elastomeric band varies, e.g., by varying the thickness of the bond, from one end of the balloon to the other to allow progressive incremental inflation of the balloon. The elastomeric band has uniform elasticity over the portion of the balloon on which it is disposed. The elastomeric band is disposed only over a center region of the balloon and divides the balloon into a proximal and a distal region. The tubular prosthesis is a stent. The balloon is substantially nondistendible. The constraint is an axially slidable sheath which surrounds the balloon, the sheath being formed of a low coefficient of friction polymer. The polymer is teflon. The balloon has an inflatable portion corresponding to the length of the prosthesis and the balloon and prosthesis have a length of about 5 cm or more. The balloon and prosthesis have a length in the range of about 8–12 cm. The prosthesis includes a clot inducing fabric. The prosthesis is folded around the balloon and constraint. The catheter includes a single lumen for injection of the inflation fluid. The inflation lumen includes an inflation port for directing fluid into the balloon, the port located at a region corresponding to a portion of the balloon not initially restrained by the constraint.

In another aspect, the invention features a balloon catheter having an inflatable balloon on its exterior. The balloon is inflatable by injection of fluid through a lumen in the catheter. The balloon is initially partially radially restrained against inflation by a constraint which surrounds the balloon. The constraint is capable of constraining the balloon so that it may be progressively incrementally inflated.

Embodiments may include one or more of the features discussed above with respect to prosthesis delivery systems. Particular embodiments may include one or more of the following. The balloon is substantially nondistendible. The constraint is an axially slidable sheath which surrounds the balloon, the sheath being formed of a low coefficient of friction polymer. The polymer is teflon. The sheath includes an extension to proximal portions of the catheter for controlling the axial location of the sheath. The sheath is adapted to slide axially in response to pressure in the balloon.

In another aspect, the invention features a method of expanding a tubular prosthesis with a balloon catheter. The method includes providing a balloon catheter having an inflatable balloon on its exterior. The balloon is inflatable by injection of fluid through a lumen in the catheter. The balloon is initially partially radially restrained against inflation by a slidable sheath which surrounds the balloon. The sheath is adapted to slide axially along the balloon onto the catheter shaft in response to a pressure in the balloon such that the balloon may be progressively incrementally inflated. A tubular prosthesis is disposed on the catheter over at least a portion of the balloon and a portion of the constraint. The tubular prosthesis has a contracted condition and an expanded condition. The tubular prosthesis is initially disposed on the catheter in the contracted condition. The method further includes inflating the balloon such that an unrestrained portion of the balloon inflates first and causes a portion of the tubular prosthesis disposed over the unrestrained portion to expand and progressively incrementally inflating the constrained portion of the balloon causing a portion of the tubular prosthesis disposed over the restrained portion of the balloon to be progressively incrementally expanded.

In another aspect, the invention features a method of expanding a tubular prosthesis with a balloon catheter. The method includes providing a prosthesis delivery package having a balloon catheter having an inflatable balloon on its exterior. The balloon is initially partially radially restrained against inflation by an elastomeric band which surrounds the balloon and is inflatable by injection of fluid through a lumen in the catheter. The elastomeric band is disposed over a significant length of the balloon and has a non-uniform thickness such that the elastomeric band progressively expands with incremental increases in pressure and allows the balloon to be progressively incrementally inflated. A tubular prosthesis is disposed on the catheter over at least a portion of the balloon and a portion of the constraint. The tubular prosthesis has a contracted condition and an expanded condition. The tubular prosthesis is initially disposed on the catheter in the contracted condition. The method further includes inflating the balloon such that an unrestrained portion of the balloon inflates first and causes a portion of the tubular prosthesis disposed over the unrestrained portion to expand and progressively incrementally inflating the constrained portion of the balloon causing a portion of the tubular prosthesis disposed over the restrained portion of the balloon to be progressively incrementally expanded.

In another aspect, the invention features a method of expanding a tubular prosthesis using a balloon catheter. The method includes providing a balloon catheter having an inflatable balloon on its exterior. The balloon is cinched in a central region with an elastic band and a tubular prosthesis is disposed on the catheter over at least a portion of the balloon and the elastic band. The tubular prosthesis has a contracted condition and an expanded condition. The tubular prosthesis is initially disposed on the catheter in the contracted condition. The method further includes inflating a first end of the balloon, the inflation causing the tubular prosthesis contacting the first end to expand, then inflating a second end of the balloon, the inflation causing the tubular prosthesis contacting the second end to expand, and finally inflating the central region of the balloon, the inflation causing the tubular prosthesis contacting the central region to expand.

In another aspect, the invention features a method of performing angioplasty using a balloon catheter. The method includes providing a balloon catheter having an inflatable balloon on its exterior. The balloon is initially partially radially restrained against inflation by a slidable sheath which surrounds the balloon and is inflatable by injection of fluid through a lumen in the catheter. The sheath is adapted to slide axially along the balloon onto the catheter shaft in response to pressure in the balloon such that the balloon may be progressively incrementally inflated. The method further includes inflating an unrestrained portion of the balloon by injecting fluid into the balloon through a lumen in the catheter and then inflating a restrained portion of the balloon by injecting additional fluid into the balloon through the lumen such that the pressure of the fluid inside the balloon incrementally slides a restraining sheath off of the balloon, allowing the balloon to progressively incrementally inflate.

In another aspect, the invention features a system for performing valvuloplasty. The system includes a balloon catheter having a balloon formed substantially of a nondistendable polymer, inflatable to at least 15 mm diameter, and being capable of being wrapped about the catheter to small diameters when in the deflated state. The system also includes a separate inflation control constraint which substantially surrounds the balloon and is expandable by deformation by application of inflation pressures to the balloon, the constraint being constructed to require higher inflation pressures to expand proximal portions than distal portions.

Embodiments may include one or more of the following. The balloon is capable of inflation to pressures of about 8 atmospheres or more before burst. The polymer is PET. The constraint is formed of an elastomeric material. The constraint has a smooth outer profile when the balloon is in the deflated state. The thickness of the constraint is less in the distal portions than in portions proximally adjacent thereof. The thickness of the constraint is greater in a middle portion adjacent the distal portion, than in a proximal portion. The portion adjacent the distal portion is not expandable at inflation pressures below about 3 atm.

Embodiments may also include one or more of the following. The system includes an inflation mechanism for injection of fluid through a lumen in the catheter to inflate the balloon, and the constraint and the inflation mechanism are cooperatively constructed. The system requires a first rapid fluid delivery mode to permit deformation of the distal portions of the constraint and expansion of distal portions of the balloon by low inflation pressures and to prevent higher inflation pressures sufficient to deform the constraint in portions proximally adjacent to the distal portions and, the constraint and mechanism further constructed to include a second high pressure fluid delivery mode to permit deformation of the constraint in the proximally adjacent portions and expansion corresponding portions of the balloon by application of higher pressures. In embodiments, the inflation mechanism is a syringe with a piston that can be operated to deliver inflation fluid by free sliding, in the first mode and by providing mechanical advantage in the second mode. The portion proximally adjacent the distal portion is not deformable below inflation pressures below about 3 atm, and operation in the first fluid delivery mode is not capable of delivering pressures above about 3 atm.

In another aspect, the invention features a method of performing valvuloplasty. The method includes providing a balloon catheter having a balloon inflatable to at least 15 mm diameter, formed substantially of a nondistenable polymer and being capable of being wrapped about the catheter to small diameters when in the deflated state. A separate inflation control constraint is provided which substantially surrounds the balloon and is expandable by deformation by application of inflation pressure to the balloon, the constraint being constructed to require higher inflation pressures to expand proximal portions than distal portions. An inflation mechanism is provided for injection of fluid through a lumen in the catheter to inflate the balloon. The constraint and the inflation mechanism are cooperatively constructed to include a first rapid fluid delivery mode to permit deformation of the distal portions of the constraint and expansion of distal portions of the balloon by low inflation pressures attainable and to prevent higher inflation pressures sufficient to deform the constraint in portions proximally adjacent to the distal portions and, the constraint and mechanism further constructed to include a second high pressure fluid delivery mode to permit deformation of the constraint in the proximally adjacent portions and expansion of corresponding portions of the balloon by application of higher pressures. The method also includes delivering the balloon into the body and positioning the balloon at a location distal of an afflicted valve, delivering inflation fluid using the first mode to deform the distal portion of the constraint and inflate a corresponding distal portion of the balloon, withdrawing the balloon proximally with the distal end of the balloon in the expanded state until resistance is felt, delivering inflation fluid using the second mode to deform the proximally adjacent portion of the constraint and inflate a corresponding portion of the balloon, the inflation pressure being sufficient to dilate the afflicted valve, deflating the balloon, and removing the catheter from the body.

In another aspect, the invention features a system for controlled deployment of an expandable medical device. The system includes a balloon catheter having a balloon formed substantially of a nondistendable polymer, and being capable of being wrapped about the catheter to small diameters when in the deflated state, and a separate inflation control constraint which substantially surrounds the balloon and is expandable by deformation by application of inflation pressures to the balloon, the constraint being constructed to require higher inflation pressures to expand a first portion than a second portion. In embodiments, the system also includes an inflation mechanism for injection of fluid through a lumen in the catheter to inflate the balloon. The constraint and the inflation mechanism are cooperatively constructed to include a first, rapid fluid delivery mode to permit deformation of the first portion of the constraint and expansion of a first portion of the balloon by low inflation pressures and to prevent higher inflation pressures sufficient to deform the constraint in the second portion and, the constraint and mechanism are further constructed to include a second, high pressure fluid delivery mode to permit deformation of the constraint in the second portion and expansion of the corresponding portion of the balloon by application of higher pressures.

The inventions have many advantages. For example, it is often important to accurately position a prosthesis so that it is properly centered about the diseased area with the ends anchored on healthy tissue on either side of the area. Often, there is only a very short segment of healthy lumen on which the ends of the prosthesis may be anchored.

The accuracy of stent positioning, particularly with long prostheses, is affected by the unpredictable nature of balloon inflation. A balloon will sometimes begin to inflate from the proximal end and sometimes from the distal end. Since expansion of a stent often results in contraction of the stent length, an irregular, unpredictable expansion introduces more uncertainty in the placement of the ends of the stent. In aspects of the invention, a predictable, controlled inflation and prosthesis expansion is achieved by using constraints.

Another problem that can arise while positioning balloon expandable prostheses, again especially those of considerable length and when using nonelastic balloons, is that, after expansion, the balloons do not deflate to their original profile but form folds or "wings" which can be quite rigid. If the balloon must be deflated and moved axially to expand an unexpanded portion of the stent, these wings can drag on the stent and dislodge it. According to aspects of the invention the balloon's length is sized to match the length of the prosthesis and the balloon is inflated only one time to fully expand of the prosthesis. In embodiments, select portions of the balloon are sequentially inflated, as if the catheter carried multiple balloons, yet the system need only include a simple, single inflation lumen catheter.

In angioplasty, a balloon catheter is used to widen an area of a lumen that is occluded, e.g., an artery occluded by plaque or intimal proliferation or a heart valve. The improved control over balloon inflation provided by this invention can improve the results which may be obtained in this area as well.

Other aspects, features and advantages follow.

DESCRIPTION OF THE PREFERRED EMBODIMENTS STRUCTURE

Figure 1:
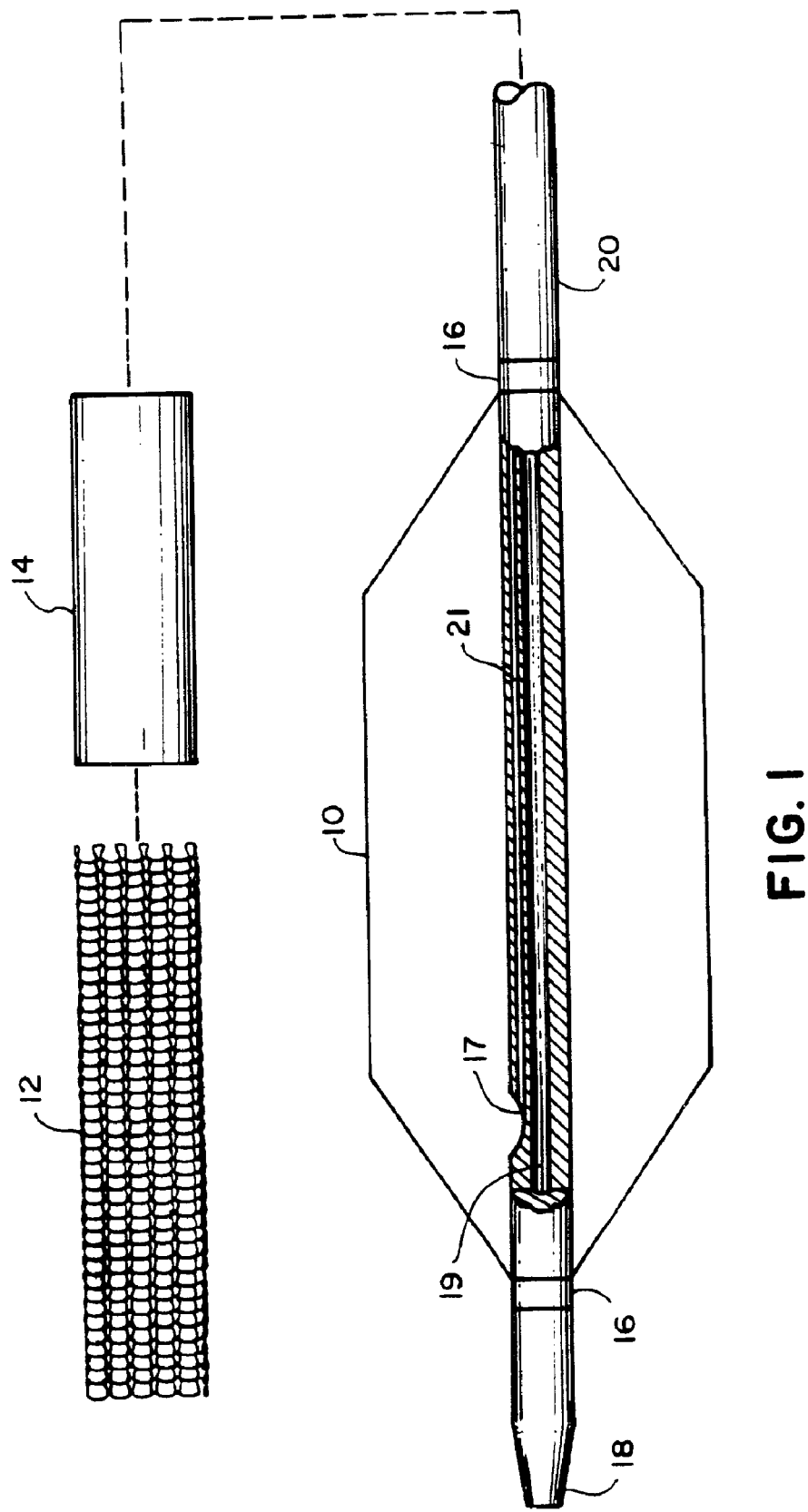
FIG. 1 is a side view of components of an embodiment of the invention, showing a balloon catheter (in partial cross-section), a constraint, and a stent.
Figure 2:
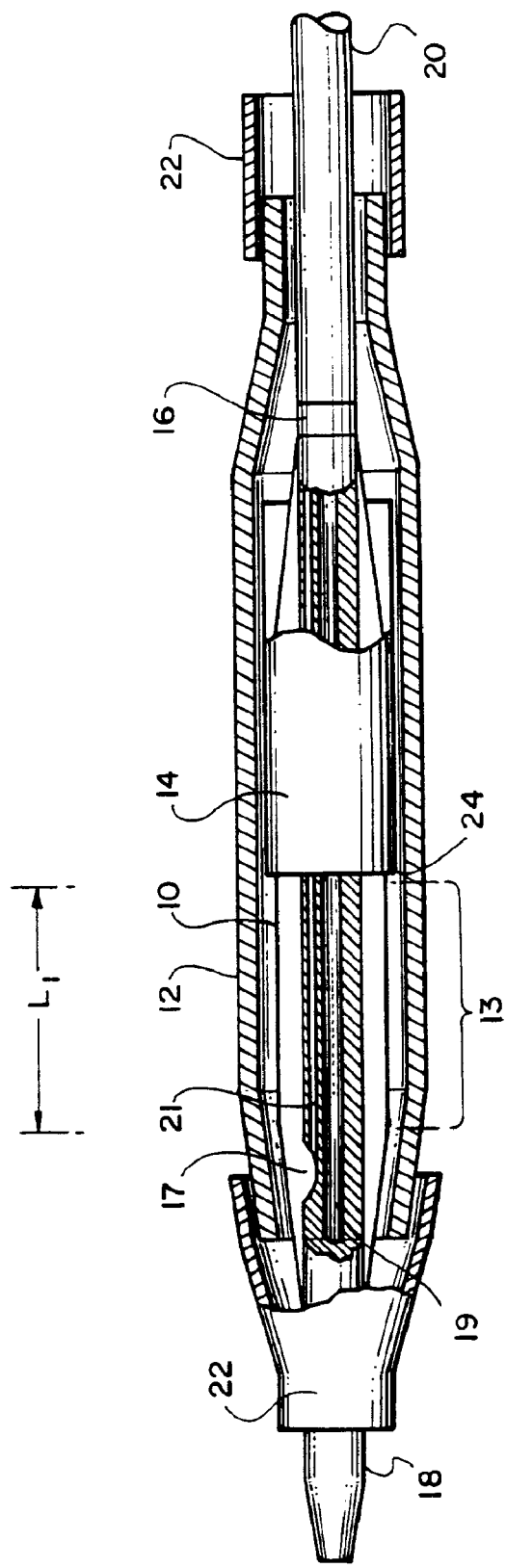
FIG. 2 is primarily a cross-sectional side view, with partial side view, of the embodiment of FIG. 1 in an assembled state prior to inflation of the balloon.

Referring to FIGS. 1 and 2, an embodiment of the invention for placement of an aortic graft includes a vascular catheter 20 carrying a balloon 10, an inflation constraint 14 in the form of an annular sheath, and a tubular prosthesis 12. Referring particularly to FIG. 2, for delivery into the body, balloon 10 is folded around the catheter body and constraint 14 is positioned so that a short distal portion 13 of the balloon remains unconstrained. Prosthesis 12, in a small diameter condition, is then slipped over this assembly such that it is disposed above the unconstrained distal portion 13 of the balloon and the constraint over the more proximal portions of the balloon. The prosthesis is held in place on both ends by sleeves 22. The balloon can be inflated by the introduction of inflation fluid through an inflation lumen 21 which communicates with the interior of the balloon via an inflation port 17.

As will be discussed in more detail below, controlled introduction of an initial volume inflation fluid to the balloon causes inflation of the unconstrained distal portion of the balloon and expansion of the corresponding distal portion of the prosthesis, while the proximal portions of the prosthesis remain in the small diameter state because the constraint prevents inflation of the proximal portions of the balloon. After inflating the distal unconstrained portion, introducing further inflation fluid to the balloon produces an axial force on the distal end of the constraint, causing it to slide proximally to expose proximal portions of the balloon, which, once free of the constraint, inflate and expand corresponding portions of the prosthesis.

Inflation constraint 14 is a tubular member of which is shorter than the balloon, e.g., extending about half of the balloon length. The inner diameter of constraint 14 is about equal to the folded profile of the balloon, which is about 3 mm in this embodiment. The friction fit between the constraint and balloon is sufficient such that the constraint will not move prior to balloon inflation, e.g., during loading of the stent or while the catheter assembly is being inserted into the patient. Yet, the friction is not so great as to prevent axial sliding of the constraint in response to axial forces on the distal end of the constraint which are created during inflation of distal portions of the balloon. The constraint is preferably made of a low friction material such as TEFLON (low friction TFE TEFLON, available from E.I. Dupont DeNemours Corp., Wilmington, Del.). The low friction inner surface of the constraint, in contact with the balloon 12, facilitates retraction of the sheath during balloon inflation. The constraint and/or the balloon may also include a lubricant to reduce friction. The inner diameter of the constraint is sufficiently large so it will slide onto proximal portions of catheter 20 upon full expansion of balloon 10 and can thus be removed from the body with the catheter after implanting the prosthesis. The wall thickness of the constraint typically ranges from five to seven thousandths of an inch, and preferably is as small as possible so that the overall diameter of the assembled product may be kept small. The thin wall of the constraint allows the pressure of the balloon to cause the distal end of the constraint to flare out slightly, which aids retraction.

The constraint is positioned on the balloon so that a distal portion 13 is not constrained. The length of the unconstrained distal portion is sufficient to allow some initial expansion of the balloon. Preferably, the length of the unconstrained portion is sufficient so that the initial expansion of the balloon will expand the distal end of the prosthesis to engage the lumen wall distal of a diseased area. The length of portion 13 may correspond, for example, at least to the expanded diameter of the prosthesis. In embodiments, for a stent with an expanded diameter of about 25 mm, the distal end 24 of the constraint is positioned, $L_1$, about 4 to 6 cm, e.g. 5 cm from the distal end of the balloon. For a balloon having a 10 cm length (inflating to full expanded diameter) and balloon sleeves of about 1.5 cm, the constraint is about 6 cm in length and initially positioned to cover substantially the length of the proximal sleeve and the proximal 4.5 cm of the balloon, leaving the distal 5.0 cm of the balloon and the 1.5 cm length of the distal sleeve unconstrained and uncovered.

Balloon 10 is made of a high strength, thin-walled, oriented material such as PET, nylon, polyethylene or any other suitable commercially available angioplasty balloon material. The balloon is typically of the nondistendible, non-elastic type that can withstand high pressures (e.g. 2 to 20 atm) and does not substantially expand beyond a diameter determined in manufacture even in response to excessive pressure. This property, as will be discussed below, facilitates controlled retraction of the constraint 14. The wall thickness of the balloon is, e.g., one thousandth of an inch. The balloon length and inflated diameter are dictated by the size of the lumen and the prosthesis which is being implanted. For example, to implant a prosthesis in an aorta, the balloon length is typically in the range of 8 to 12 cm and the inflated diameter between 20 and 30 millimeters, with deflated folded profiles at about 3 mm. This may vary depending on the age and size of the patient. The invention is particularly applicable to prostheses and balloons of extended length, that is those greater than about 3 cm, e.g., 5 to 15 cm, since at this length balloon expansion may become irregular without the constraint. Balloon sleeves 16 are integral with the balloon and are attached to catheter shaft 20 by epoxy, e.g., of the type cured with ultraviolet radiation (available from Loctite, (Medical Products Group), Newington, Conn.). Construction of the balloon and sleeves may be, for example, according to Noddin, U.S. Pat. No. 4,963,313, the entire contents of which is hereby incorporated by reference.

Figure 8:
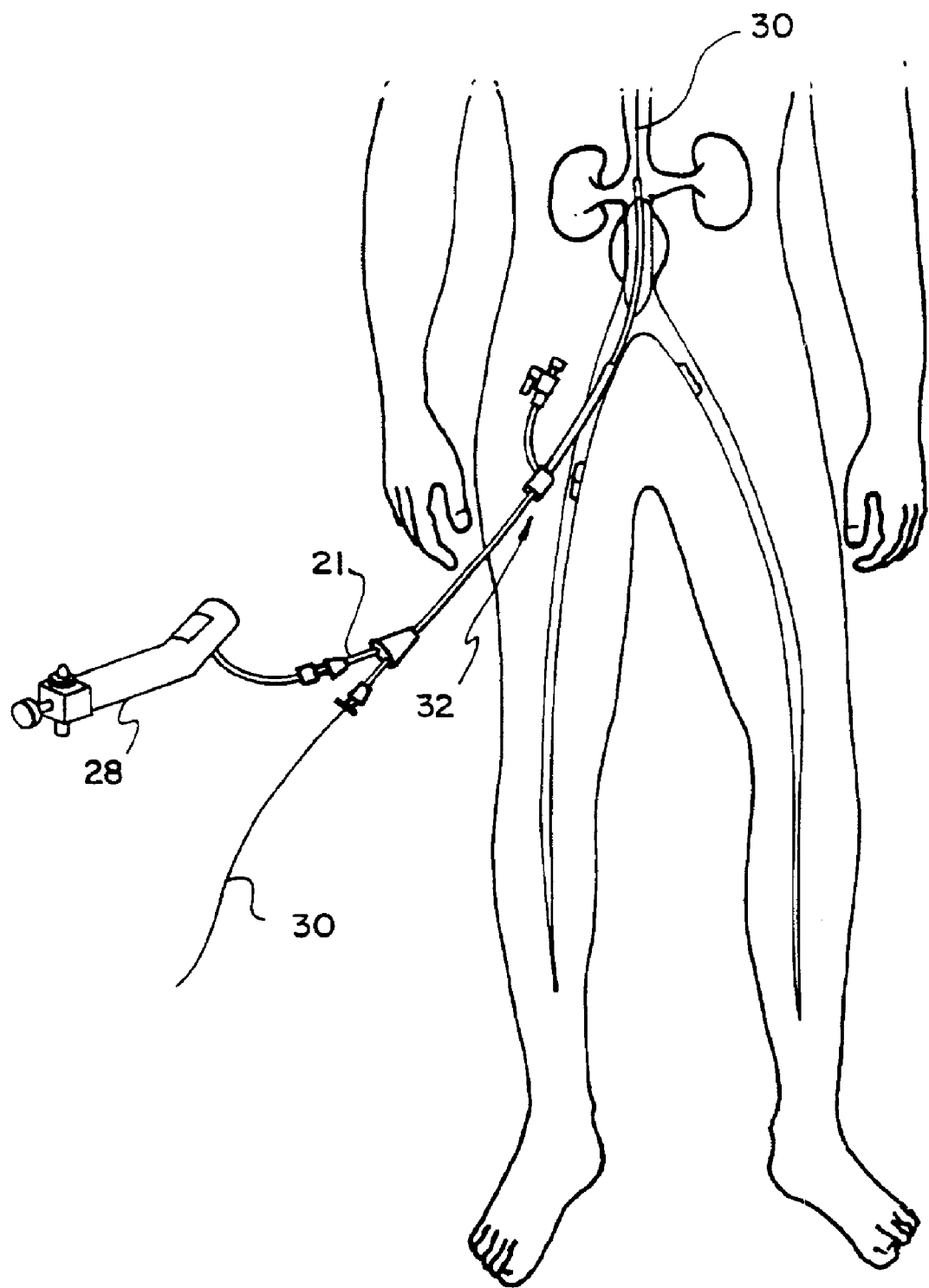
FIG. 8 is a view of the embodiment of the invention shown in FIGS. 1–7, in use in a human.

Catheter shaft 20 (diameter 0.094 inch) is made from plastic such as nylon, e.g., elastomeric nylon (PEBAX, Atochem Corp., Philadelphia, Pa.), PVC, polyurethane, or any other suitable plastic. Inflation lumen 21 within catheter 20 extends from near the distal end of the balloon to inflation device 28 (FIG. 8). The diameter of catheter shaft 20 is kept as small as possible, yet large enough to accommodate inflation lumen 21 and a guide wire lumen 19. If desired, additional lumens, such as a lumen extending through distal tip 18 for injecting fluid into an aneurysm, or a fibre optic lumen for viewing the procedure, may be included in catheter shaft 20. Distal tip 18 of catheter shaft 20 is preferably an atraumatic tip smoothly shaped to avoid puncture or abrasion of the lumen wall during entry into the body. Embodiments of the system may be constructed to allow the balloon to inflate progressively from the proximal to the distal end, by including an extension on the catheter distal of the balloon to receive the constraint on full inflation, and positioning the sheath to leave a short proximal portion of the balloon unconstrained.

Inflation lumen 21 terminates at a location along the catheter length which is not initially covered by the constraint 14. If inflation lumen 21 terminates at a point located in a portion of the balloon which is initially covered by constraint 14, the inflation rate of the balloon is decreased. Multiple ports may be skived into the inflation lumen to assist with deflating the balloon after the prosthesis has been expanded.

Prosthesis 12 is preferably a balloon expandable prosthesis including clot inducing fabric strands co-knit with metal strands as taught in U.S. patent application Ser. No. 07/912,902, filed Jul. 13, 1992, which is incorporated herein by reference. The invention is particularly suitable for use with folded fabric-containing prosthesis which can twist about the catheter if not progressively expanded. Knitted stents are particularly suitable for extended lengths because of their high flexibility which allows the stent to conform to the sometimes torturous path of the lumen. Other suitable prostheses include for example, the Strecker stent, a balloon expandable knitted stent described in U.S. Pat. No. 4,922,905; the Palmaz stent described in U.S. Pat. No. 4,776,337; and the Parodi prosthesis in which a dacron graft is sewed between two stents, as described in European Pat. App. No. 91-304988.8. All of these cases are incorporated herein by reference. Prosthesis retaining sleeves (e.g. formed of SILASTIC, Dow Corning Corp., Midland, Mich.) of suitable construction are discussed in Savin U.S. Pat. No. 4,950,227, the entire contents of which is hereby incorporated by reference.

Use

Referring to FIG. 8, the invention may be used for the treatment of aortic aneurysms. A physician accesses the femoral artery by either a cutdown or percutaneous access and bleeding is managed by an access sheath 32 equipped with a hemostasis valve such as the PINNACLE hemostasis valve (Boston Scientific Corp. of Watertown, Mass.). A guidewire 30 is passed through the access sheath into the femoral artery, through the iliac artery and into the abdominal aorta. A catheter of the invention (configured as in FIG. 2) is passed over the guide wire and positioned about the aneursym. The partially constrained balloon is inflated by attaching an inflation device 28 to a port of inflation lumen 21 on the proximal end of catheter 20. The inflation device is preferably a LEVEEN screw syringe (Boston Scientific Corp.) which enables accurate displacement of a volume at high pressures of between six and twenty atmospheres. Fluid, such as a water-saline-renographic mixture, is used to inflate balloon 10. A constrast agent, e.g., RENOGRAFIN, (Squibb Diagnostics Inc., Princeton N.J.), visible under fluoroscopy, allows the controlled inflation of the device to be monitored.

Figure 3:
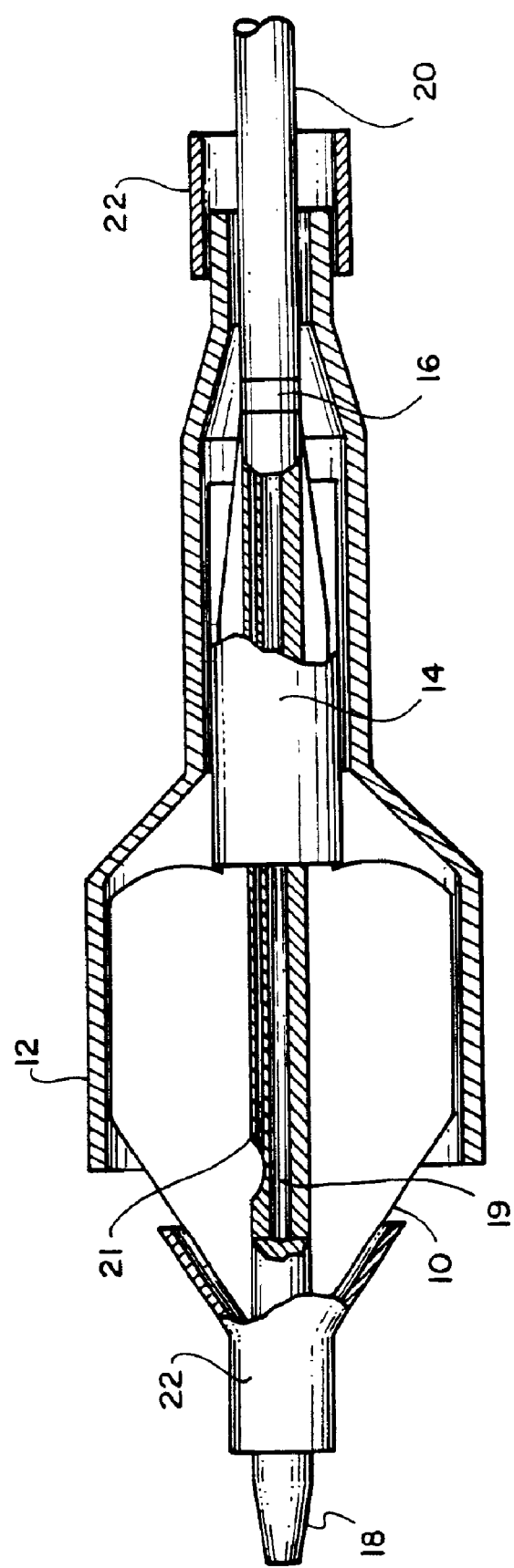
FIGS. 3–6 are views of the embodiment shown in FIG. 2, illustrating sequential stages of balloon inflation.
Figure 4:
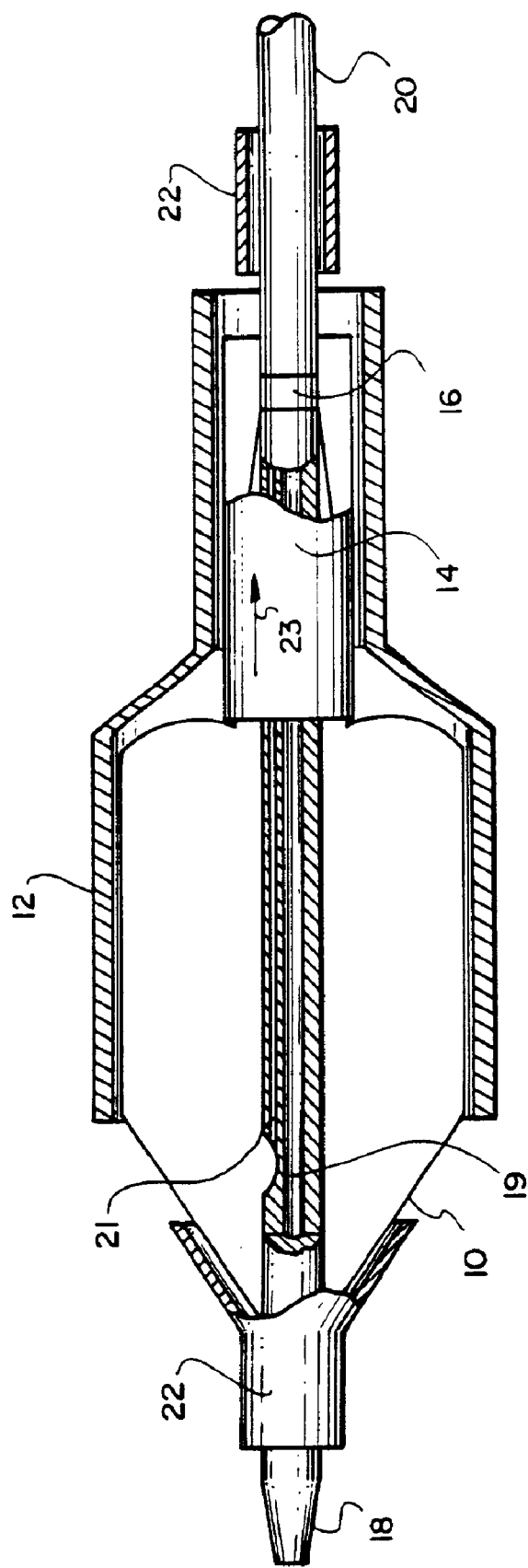
Figure 5:
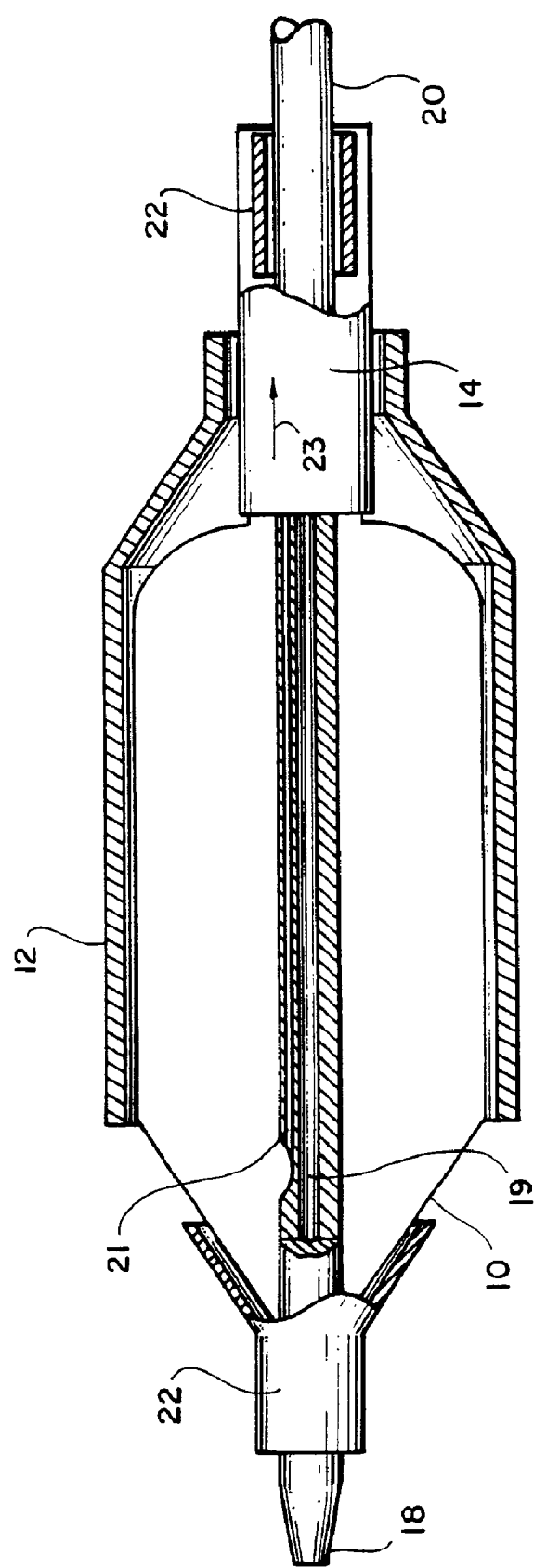

Referring to FIGS. 3–6, the prosthesis may be progressively expanded. As fluid is injected into the balloon, the distal portion of the balloon, which is not covered by the constraint 14, inflates and expands the corresponding portion of the prosthesis (FIG. 3). Because this unconstrained distal portion of the balloon is always the first part of the balloon to expand, the distal end of the prosthesis may be accurately and reliably positioned on healthy lumen tissue distal of the aneurysm. The expanded portion of the prosthesis engages the aortic wall and provides an anchor which holds the stent in place during subsequent inflation and expansion. The radial force from the pressure inside the balloon secures the distal segment of the stent in this position. (As illustrated, on expansion, the prosthesis may shrink somewhat axially, drawing this portion of the stent positioned over the balloon sleeves over the working surface of the balloon.)

Figure 6:
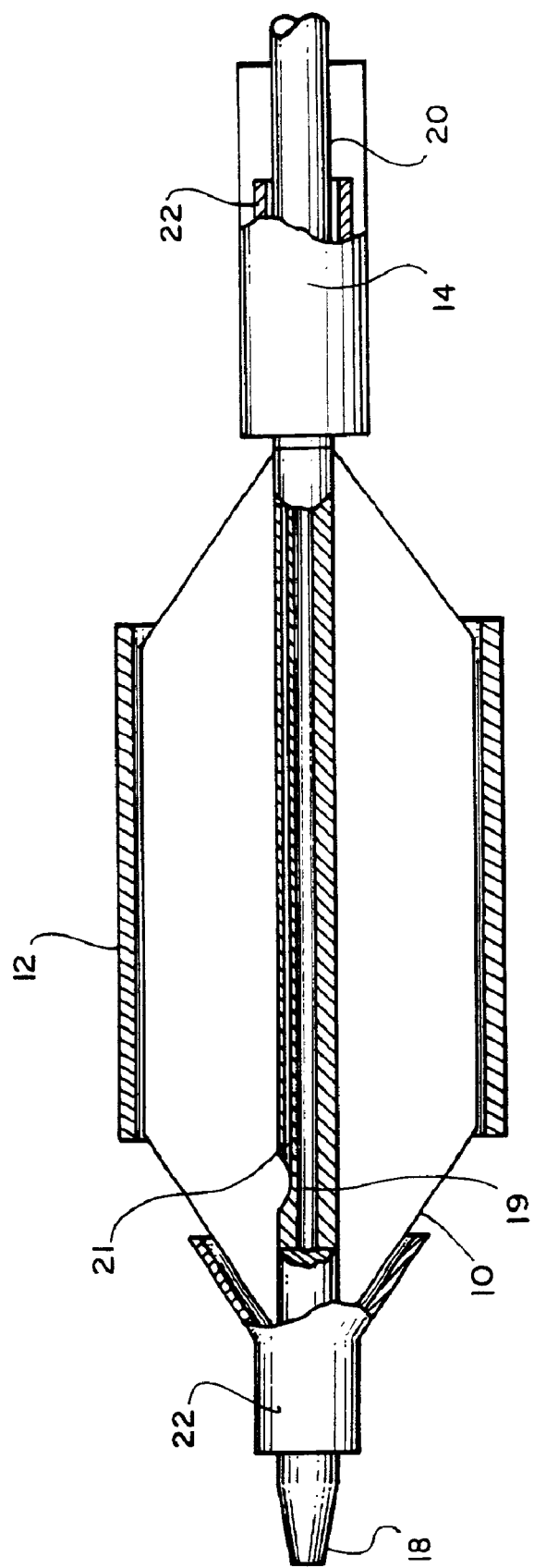

Injection of additional fluid (without prior deflation of the balloon) causes constraint 14 to slide (arrow 23) axially proximally (FIGS. 4 and 5), allowing expansion of the proximal portions of the prosthesis in an automatic, progressive, and controlled manner. After continued inflation, constraint 14 is positioned over the catheter body and is no longer in contact with balloon 10 (FIG. 6). (Again, axial contraction of the stent draws the proximal end distally during expansion.) Complete inflation of the balloon allows complete expansion of the stent so that the proximal end of the stent will be secured to healthy lumen tissue proximal of the aneurysm. Careful introduction of fluid using, e.g., a screw syringe, allows the length of balloon inflated, and the length of the prosthesis expanded, to be carefully controlled. For example, each turn of the syringe may move the constraint an additional distance, e.g., 1 mm, exposing and inflating a corresponding length of the balloon.

Figure 7:
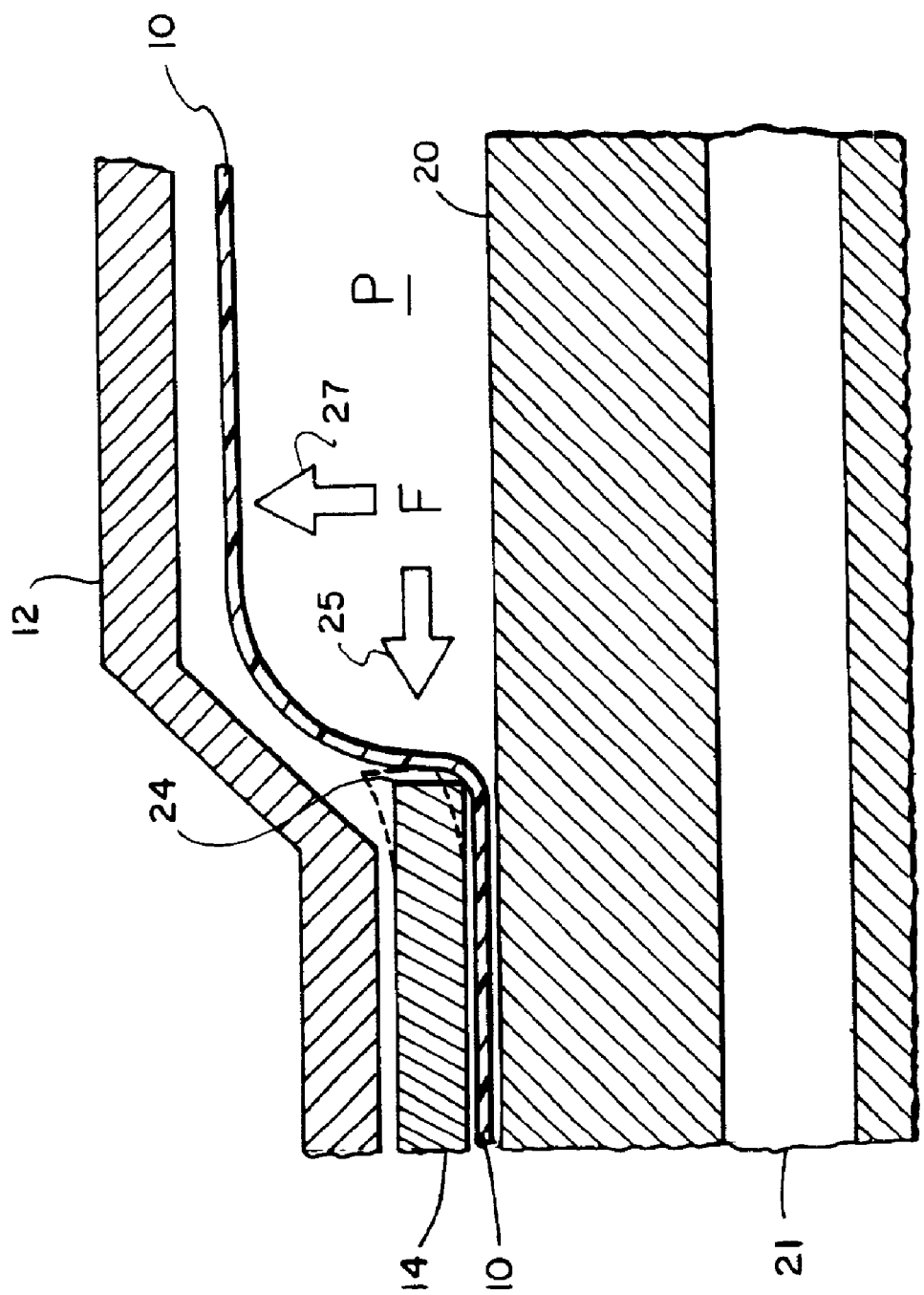
FIG. 7 is an enlarged, cross-sectional view of a portion of the embodiment in FIG. 2, showing forces applied during balloon inflation.

Referring to FIG. 7, the constraint-balloon interface is illustrated during inflation of the balloon. The pressure P inside of the balloon 10 produces a force in both the axial and radial directions (block arrows 25, 27, respectively). The radial force in the unconstrained region is resisted by the nonelastomeric material of the inflated portion of the balloon. An axial force is applied by the balloon to the distal end 24 of constraint 14. This axial force is sufficient to overcome the frictional force between the folded portions of the balloon 10 and the constraint 14 and cause constraint 14 to slide axially along the catheter away from the expanded portions of the balloon and exposing additional balloon material formerly disposed under constraint 14. This wedging action thus causes the constraint to incrementally allow the balloon to inflate and the prosthesis to expand. The pressure P in balloon 10 may also cause the end 24 of constraint 14 to flare radially outward (phantom) and increase the wedging action at the interface.

As discussed above, it is important that the frictional forces between the constraint and the balloon be selected so that the constraint can slide axially during balloon expansion. A nonelastic balloon material is preferable for this purpose since the material does not substantially stretch when placed under pressure. The frictional forces between the folded portions of the balloon and constraint do not become excessive during inflation since the folded nonelastic material under the constraint does not stretch to accept large volumes of inflation fluid which were introduced at the distal end. Nor do the folded portions conform to the inner wall of the constraint, which can increase surface area contact. The axial pressure against the distal end of the constraint is increased since the distal inflated portion of the balloon does not stretch in response to increased pressure.

Other Embodiments

Figure 9:
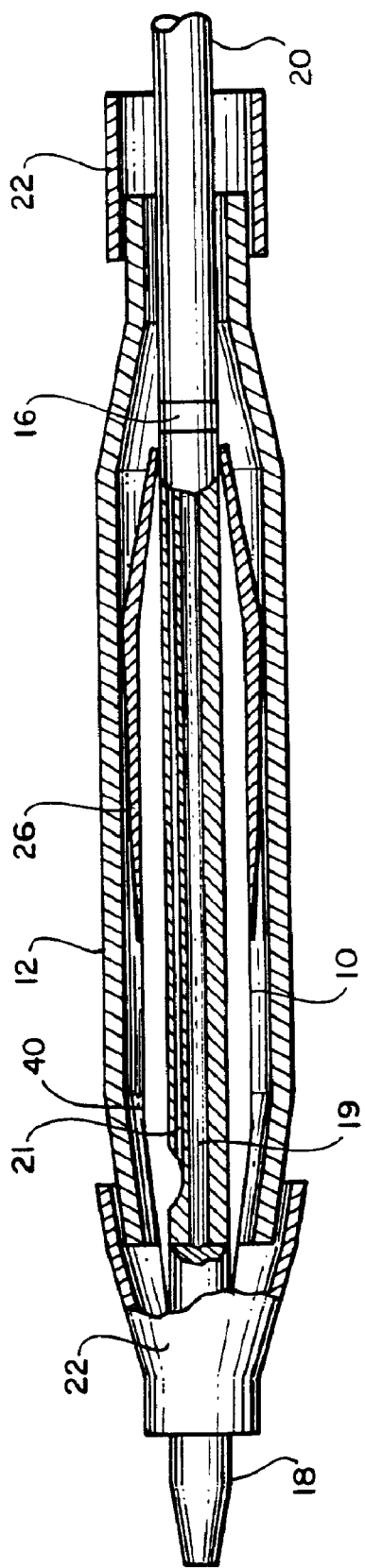
FIG. 9 is a cross-sectional view of another embodiment of the invention.

Referring to FIG. 9, in another embodiment, an elastic, nonaxially moveable constraint 26 is used in place of nonelastic constraint 14 discussed above, to provide resistance to inflation of the regions of the balloon over which it is disposed. The elastic resistance causes the section 40 of the balloon which is not covered by the elastic constraint to inflate first. Once this portion is inflated, as the pressure inside the balloon is raised to exceed the resistance provided by the elastic constraint, the constrained region of the balloon inflates. In this embodiment, preferably a single inflation lumen is provided at a location corresponding to the portion of the balloon 40 that is to be inflated first.

As shown, the constraining force of the constraint 26 may be varied by varying the thickness of the constraint along the axial direction so that the balloon progressively inflates from one end to the other. (In embodiments, the elastic constraint may extend the full length of the balloon.) Alternatively, a sequence of separate elastic constraints of differing resistance can be disposed axially along the length of the balloon so that individual regions sequentially inflate.

Figure 10:
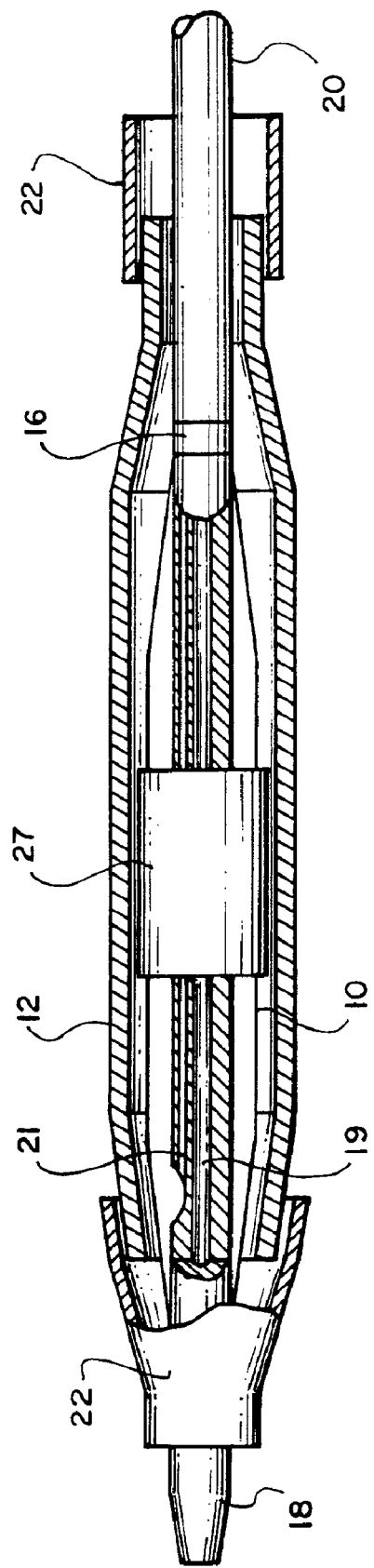
FIG. 10 is primarily a cross-sectional view of another embodiment of the invention.

Referring to FIG. 10, in another embodiment, an elastic constraint 27 is applied only to the center region of balloon. In this embodiment, the distal end of the balloon inflates first, then, once the pressure reaches a level sufficient to partially overcome the constraint, fluid channels through the constrained area into the proximal end causing it to inflate. The central region including the constraint inflates after both ends are inflated, allowing the balloon to completely inflate. The balloon catheter having a single balloon thus simulates a catheter having two balloons. The location of the inflation lumen ports can be selected in this case, to cause either the proximal and distal end to inflate first since the segment of the balloon containing the port will be the first to inflate. It is an advantage of the invention that varied portions of the balloon may be inflated as determined by the constraint, but a catheter with only a single inflation lumen is required. (Multiple deflation lumens may be used to increase deflation rate.)

In other embodiments, more than one constraint is used so that a central portion of the stent may be first expanded. In this embodiment either slidable sleeves are incrementally axially displaced from each end of the balloon by the wedging action or elastic constraints on both ends of the balloon are overcome by internal pressure in the balloon.

In other embodiments, the constraint may be such that it is axially moveable and manipulable from proximal portions of the catheter remaining outside the body. The constraint may be constructed as a sheath that runs the full length of the catheter or is controlled by a wire extending through an additional lumen in the catheter. The constraint is manually withdrawn to effect a desired length of inflation and expansion of the graft. The constraint may also initially extend over the full length of the balloon. The full-length constraint can be withdrawn axially a short distance, then the balloon inflated, allowing progressive automatic expansion of the prosthesis as the constraint slides distally or the constraint may be manually retracted a desired distance and located so only a desired length of the balloon will inflate. The catheter body may also include adjustable stops which limit the axial travel of the constraint. These stops may be adjustable from the proximal portion of the device.

Figure 11:
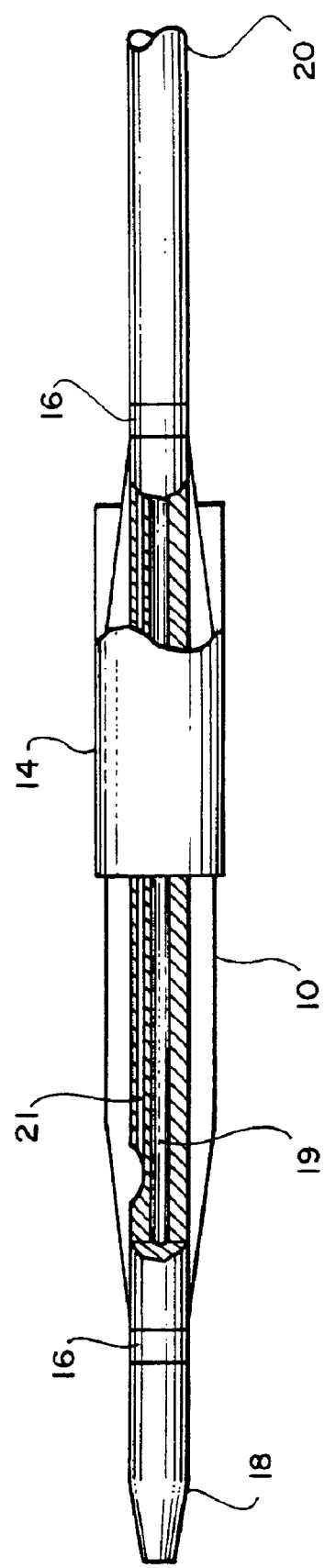
FIG. 11 is cross-sectional view of a dilation balloon catheter according to the invention.
Figure 11A:
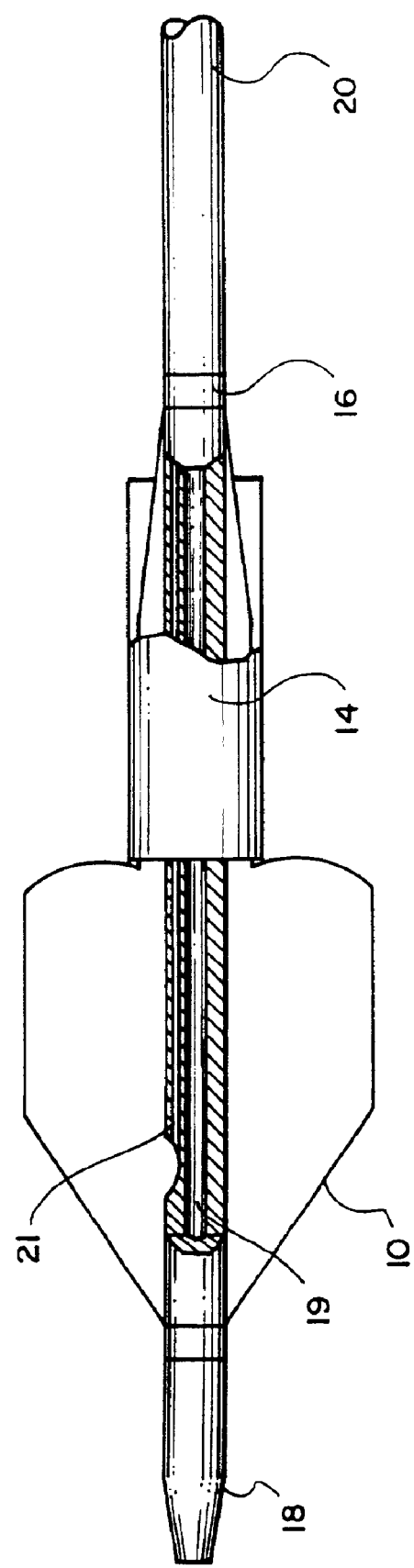
FIG. 11A a view similar to FIG. 11 with the balloon partially inflated.

Referring to FIGS. 11 and 11A, the invention may also be employed without a prosthesis to perform angioplasty, particularly percutaneous transluminal coronary angioplasty. Often, in this type of procedure, it is only necessary to expand a short segment of the artery. This embodiment is similar to that of FIG. 2, with the prosthesis and its constraining sleeves removed. The inflation balloon could be controlled as above using a constraint. Short or long regions of an artery could be selectively dilated using an adjustable stop on the catheter shaft that prevents sliding of the constraint beyond a certain distance or the constraint could be axially controllable from proximal portions of the catheter as discussed above.

Figure 12:
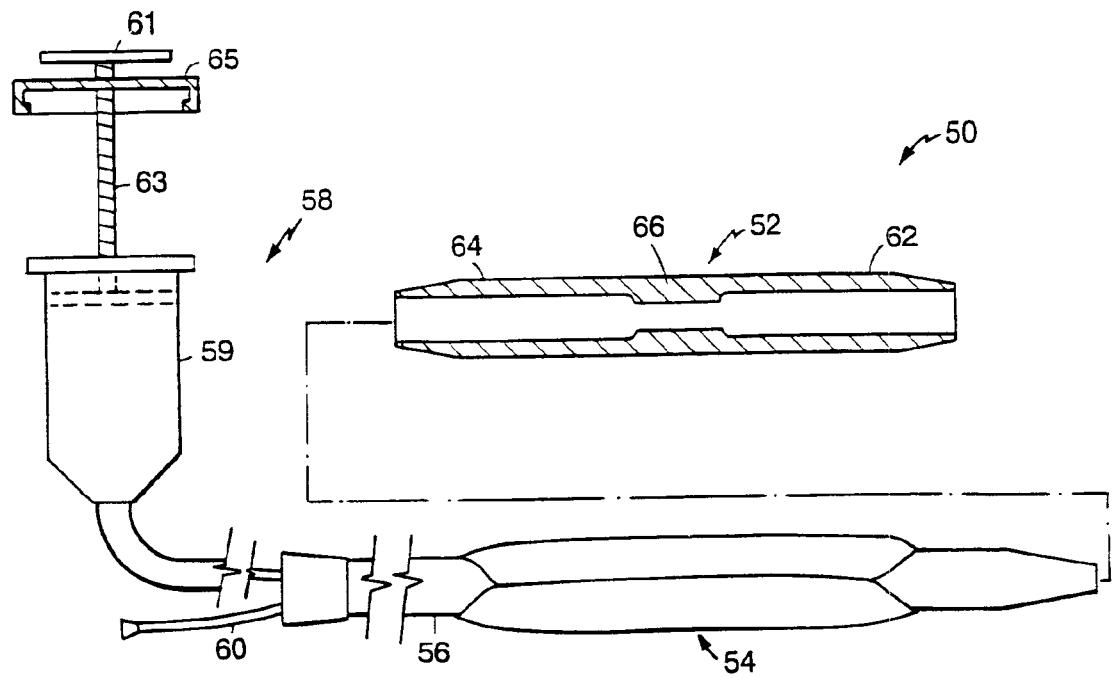
FIG. 12 is an assembly view of another embodiment of the invention.
Figure 13:
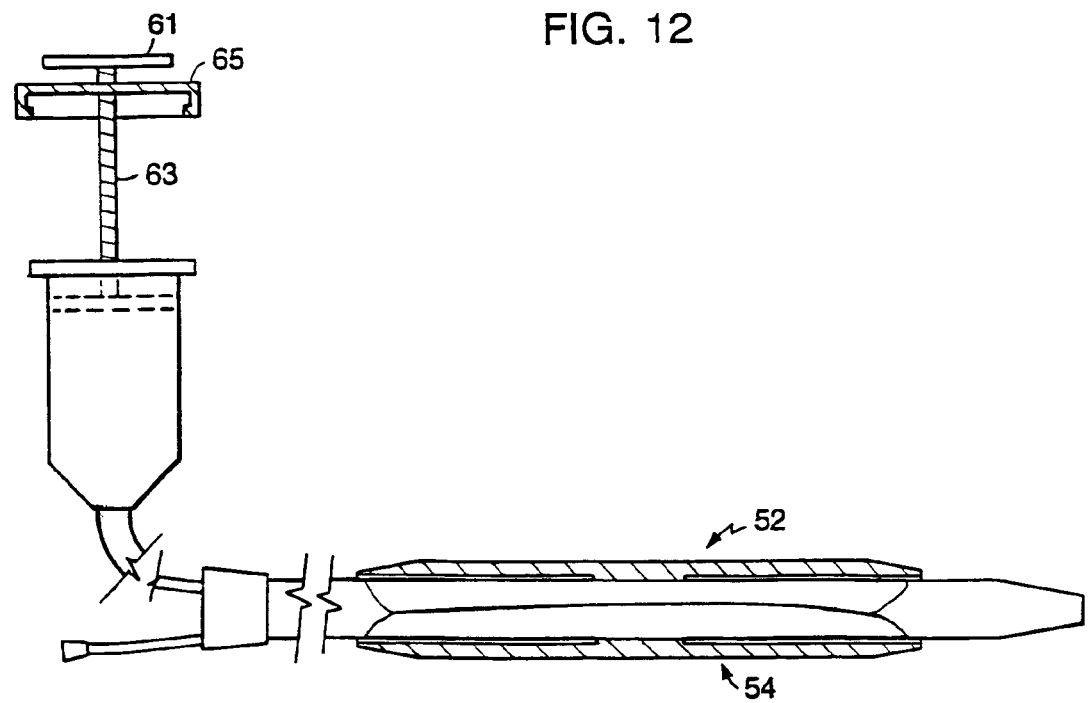
FIGS. 13–13c illustrate operation of the embodiment in FIG. 12.

Referring to FIG. 12, in another embodiment, a system 50 for dilatation, particularly in a valvuloplasty operation, includes a tubular constraint 52 (shown in cross section) which can be disposed over a balloon 54 of a balloon catheter 56 and an inflation mechanism 58 which remains outside of the body and allows the physician to controllably introduce inflation fluid through an inflation lumen (not shown) in the catheter for the purpose of controllably inflating the balloon. Referring as well to FIGS. 13–13c, with the constraint 52 positioned concentrically over the balloon 54, the physician can, by operating the inflation mechanism 58, controllably, sequentially inflate the distal 70, proximal 72, and middle portions 76 of the balloon, corresponding to distal 62, proximal 64, and middle 66 portions of the constraint.

The catheter (about 9 French) formed of, for example, nylon, has two lumens. One lumen is for delivery and withdrawal of inflation fluid; it terminates distally at a single port at a location corresponding to the distal portion of the balloon. Besides the inflation lumen, a guidewire lumen is provided which extends from a port 60 at the proximal end of the catheter to the distal end.

The balloon 54 is constructed such that it can be inflated to relatively large diameters, corresponding to the valve under treatment, and to relatively high pressures and also can be wrapped around the catheter in the deflated state to provide a low profile during delivery. A preferred balloon is made of nondistendable biaxially oriented PET with very thin walls (e.g. 0.001–0.002 inch) and which can be inflated to diameters of 15–30 mm, e.g. 20–25 mm, at pressures of 8 atm or more, and wrapped in the deflated state about a 7.5 F catheter portion to form a 9F profile. The balloon may also be made of a polymer blend of PET and selar as discussed in U.S. Pat. No. 5,306,246, issued Apr. 26, 1994, the entire contents of which is incorporated herein by reference. The length of the balloon is typically 3–5 cm.

The constraint 52 is formed of a material that can be controllably deformed depending on the level of inflation fluid pressure. Preferably, the constraint 52 is formed of an elastomeric material, such as silicone (e.g. 600–800% elongation to break) or latex. In other embodiments, the constraint may be inelastic, but plastically deformable by select balloon inflation pressures. In a particular embodiment, the constraint 52 has a distal portion 62 (e.g. 0.010 inch thick, silicone) that is thinner than the proximal portion 64 (e.g. 0.020 inch thick), which is thinner than the middle portion 66 (e.g. 0.040–0.050 inch thick). The middle portion is typically 10–15% of the overall length and the proximal and distal portion are typically of equal length. As illustrated, the outer profile of the constraint is smooth when the balloon is in the deflated state; the thickness difference results in a varying inner diameter. In embodiments, only the thickest, middle portion of the constraint engages the balloon when it is deflated and folded around the catheter (FIG. 13). This feature makes it easier to initially inflate the proximal and distal portions by allowing the balloon to unfold slightly underneath the constraint before expanding it. The middle portion does not engage the balloon with excessive force that could pinch off the flow of inflation fluid. The constraint can be manufactured separately from the balloon, e.g., by molding, and then slipped over the balloon and attached at one or both of its ends to the catheter shaft by epoxy, glue, or tying. Alternatively, the constraint may be friction fit on the balloon by the physician just prior to use. The constraint may include a safety wire attached at its proximal end that runs proximally to outside the body. The system may be provided as a kit with a balloon catheter and a set of sleeves constructed for different inflation characteristics. The constraint can also be attached to the balloon by epoxy, etc.

The inflation mechanism and the constraint are cooperatively constructed to allow a desired inflation sequence. In some embodiments, the physician can overcome the constraint and expand the distal, proximal, and middle portions by depressing a syringe plunger with a thumb (e.g. exerting a maximum of about 3 atm of pressure). The physician can monitor which portions of the balloon have been inflated by observing the volume of inflation fluid that has been delivered from the syringe.

In other embodiments, the system is constructed to require that the physician switch from one mode of fluid delivery to another mode before a portion of the balloon can be inflated. For example, the system may be constructed to permit rapid balloon positioning by inflation of the distal and proximal portions at lower pressures using thumb depression and a more careful, deliberate dilation by inflation of the middle portions to much higher pressures using a mechanical advantage.

Referring particularly to FIG. 13, the inflation mechanism 58 is preferably of the type that includes a syringe and a piston 61 which can be slid into a barrel when depressed by the physician's thumb and which also includes screw threads 63 along the shaft which are mated with a moveable set of corresponding threads 65 that can be locked to the barrel of the syringe so that the piston can also be depressed by rotation. The latter mode provides a mechanical advantage that permits inflation to higher pressures. Moreover, in the latter mode, the physician does not have to maintain manual force on the piston to keep the balloon from deflating. A suitable system is the Leveen® Inflator, available from Boston Scientific Corporation, Watertown, Mass., with a barrel capacity of about 20 cc and a barrel diameter of about 2.3 cm. A system is discussed in Leveen U.S. Pat No. 4,312,343, which is incorporated by reference. Another suitable system is the RigidFlator®, also available from Boston Scientific, in which a syringe piston can be slid or alternatively rotated to deliver inflation fluid.

Figure 13A:
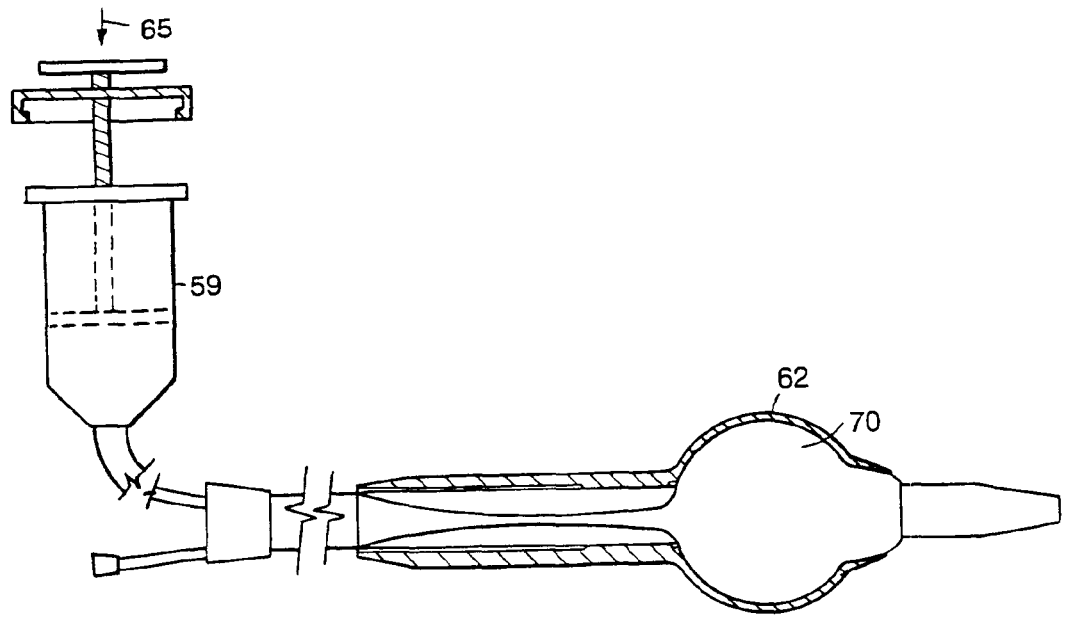

Referring particularly to FIG. 13a, the physician can depress the piston 68 with the thumb (arrow 65) to deliver inflation fluid to the interior of the balloon at a pressure of about 1–2 atm. The distal portion 70, covered by the distal portion 62 of the constraint 52, inflates first since the resistance provided by the thin distal portion of the constraint 52 is overcome by this level of inflation fluid pressure.

Figure 13B:
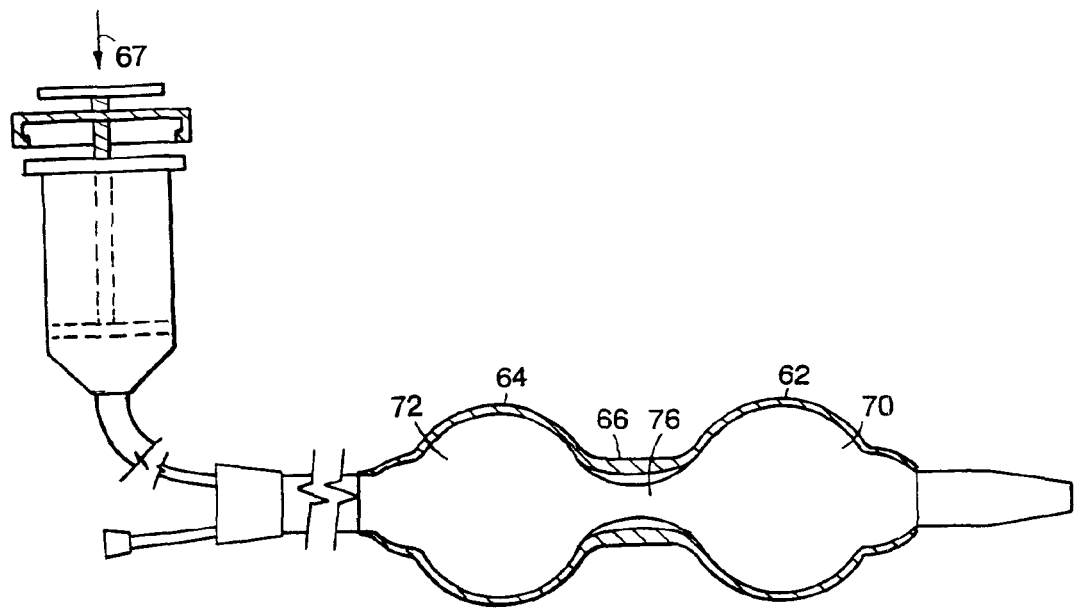

Referring particularly to FIG. 13b, by further depressing the plunger 68, with, for example, the thumb (arrow 67), the proximal portion of the balloon 72, which is covered by the proximal portion 74 of the constraint 52 is inflated. At this point, the physician is exerting about 3 atmospheres or less of pressure. The middle portion 76 of the balloon remains substantially deflated because the thick, middle portion 66 of the constraint cannot be overcome by pressure that the physician can exert with his thumb. The possibility that the middle portion of the balloon will be inflated prematurely is eliminated, since the physician cannot inflate the central portion without using a mechanical advantage upon the syringe piston. (It is preferred that the middle portion be inflated somewhat by thumb depression, e.g. about 30% of full inflation diameter, so that it is in contact with the valve under treatment before full inflation at higher pressures by the slower rotary depression delivery mode.) The physician does not have to observe external indicators such as fluid volume delivered or pressure to know that the central portion has not been expanded.

Referring to FIG. 13c, to fully inflate the middle portion 76, the moveable screw threads on the piston shaft are locked onto the barrel. Further inflation fluid can then be delivered by rotating the piston shaft into the barrel (arrow 69) to exert higher pressures, for example 3 to 8 atmospheres or more, which inflates the middle portion 76 of the balloon. (The middle portion 66 of the constraint extends outward slightly because of its greater thickness. In use, this portion of the constraint would be compressed by the valve being dilated.) After dilatation, the balloon can be rapidly deflated by unlocking the screw threads from the barrel and withdrawing the piston. The deflated balloon is urged back into a low profile position by the elasticity of the constraint 52. Since the balloon deflates in a reverse sequence as inflation, the balloon is efficiently and compactly refolded. Moreover, the constraint presents a smooth outer surface. These features aid withdrawal of the catheter after dilatation.

Figure 14:
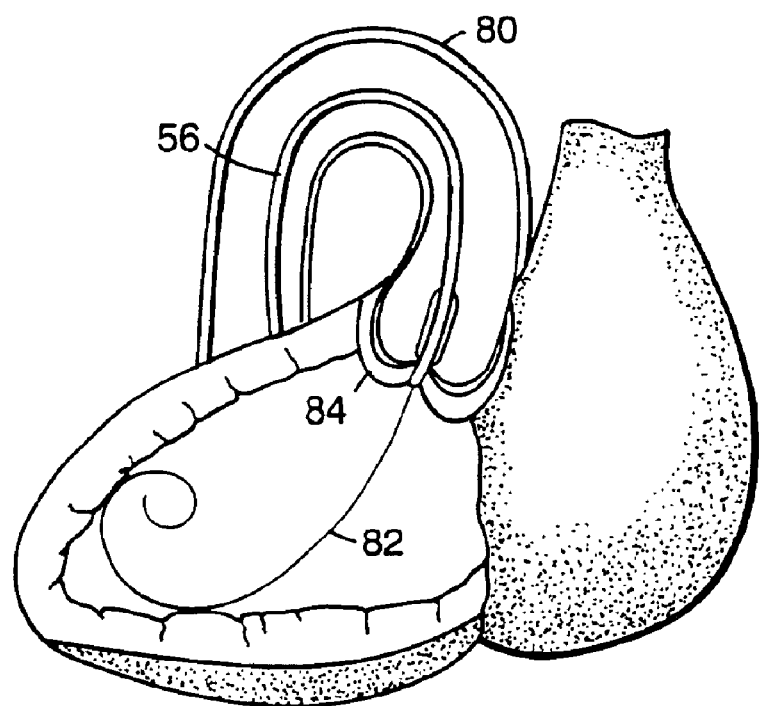
FIGS. 14–14e illustrate the use of the embodiment in FIG. 12 in a valvuloplasty operation.
Figure 14A:
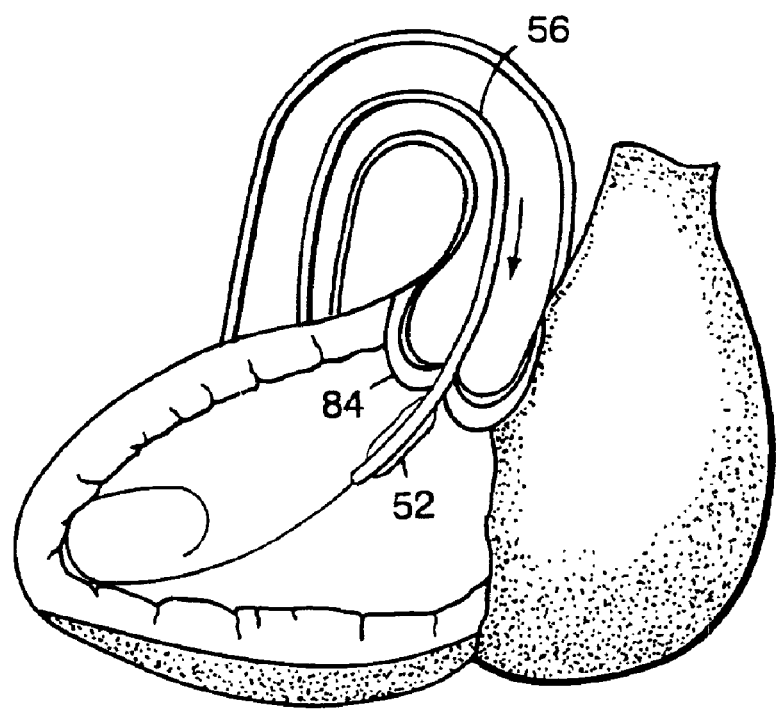
Figure 14B:
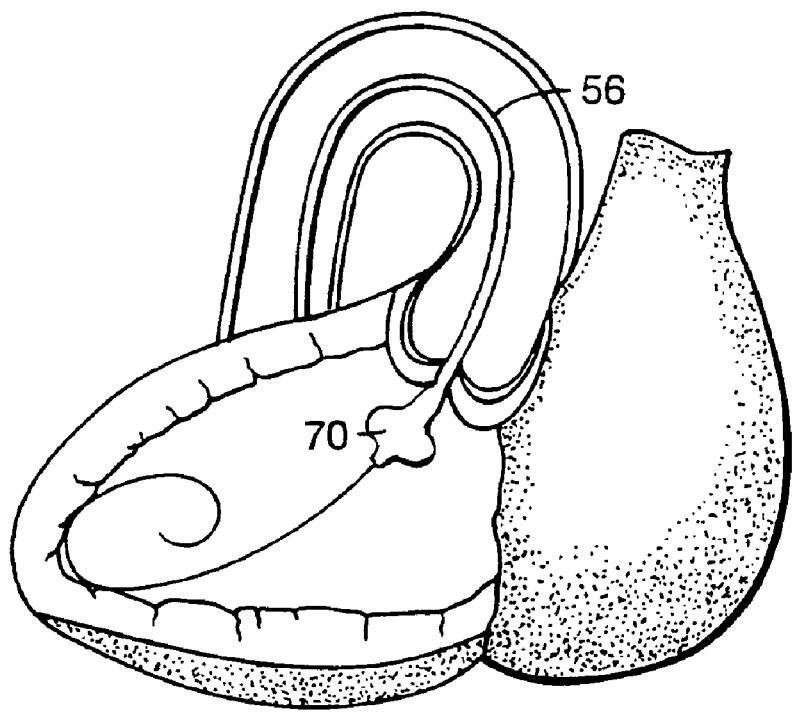
Figure 14C:
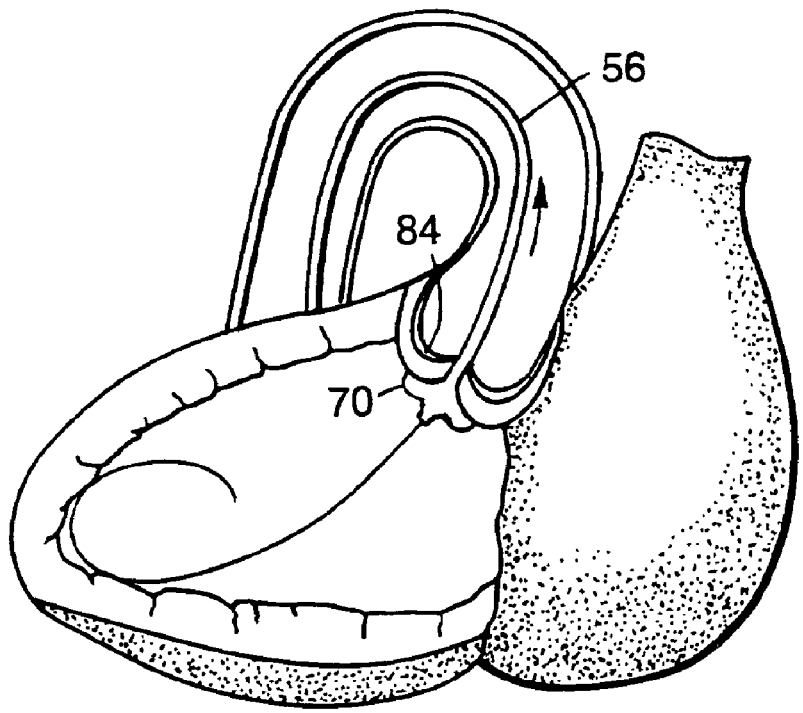
Figure 14D:
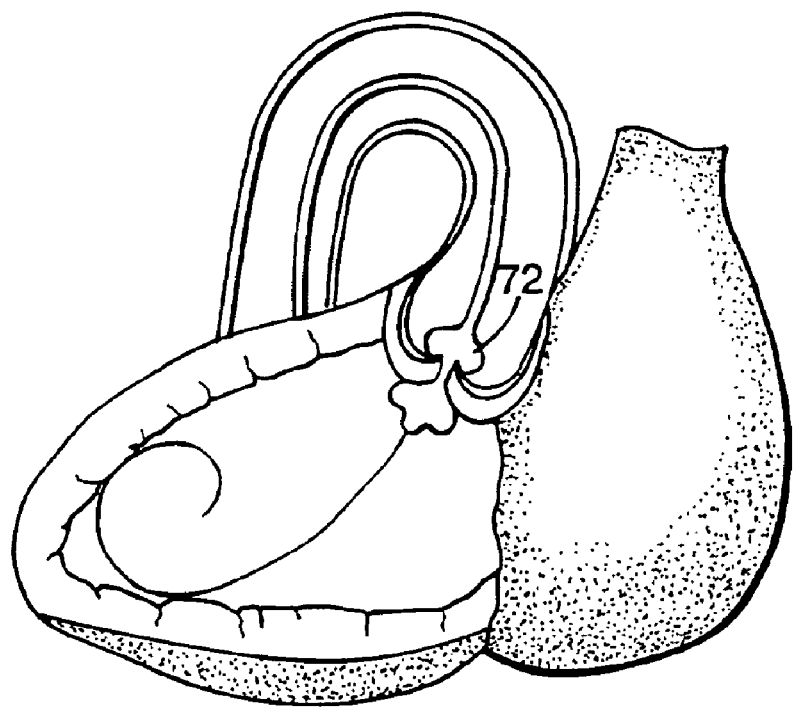
Figure 14E:
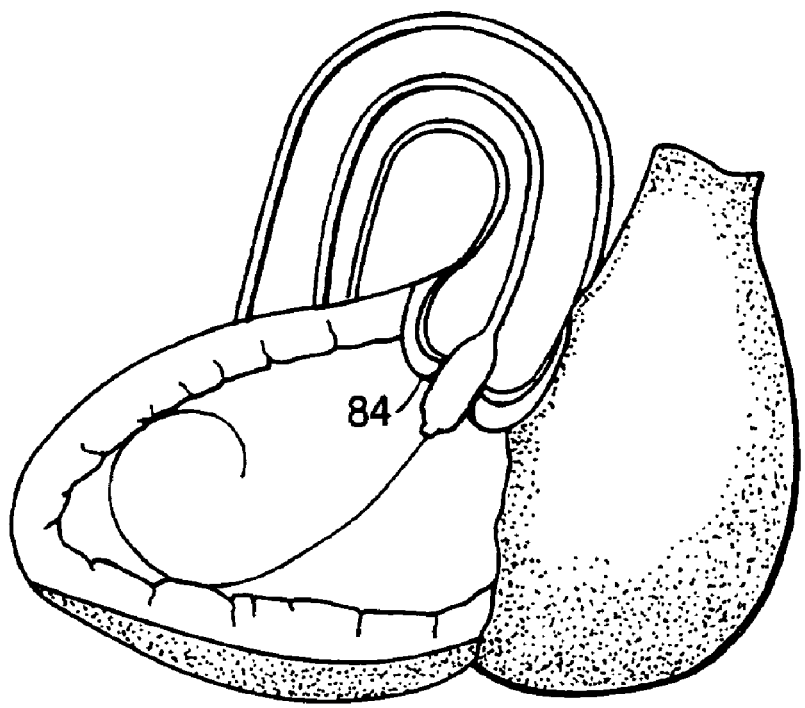

Referring to FIGS. 14–14e, a particular application for this embodiment is valvuloplasty, which is the dilatation of heart valves which fail to open naturally because of plaque build-up, or other disease, such as heart disease brought on by rheumatic fever. This example illustrates dilatation of the aortic valve, but a similar technique can be used for dilatation of the tricuspid, mitral or pulmonary valves. While the physician may view the placement and dilation using fluoroscopy, it is preferred that most of the steps be carried out quickly by feel, since obstruction of the heart by the catheter for extended periods can be dangerous for the patient.

Referring particularly to FIG. 14, the catheter 56 is delivered from the groin through the femoral artery into the aortic arch 80 over a guidewire 82 which had been previously placed in the heart. Referring to FIG. 14a, the catheter 56 is urged distally such that the constraint 52 and the balloon 54 are at a location distal to the aortic valve 84. Referring particularly to FIG. 14b, the physician then inflates the distal portion 70 of the balloon to a large diameter. Referring to FIG. 14c, the catheter 56 is then drawn proximally until the physician feels resistance as the distal portion 70 of the balloon engages the inner walls of the aortic valves. Referring to FIG. 14d, the physician then delivers further inflation fluid to inflate the proximal portion 72 of the balloon. At this point, the balloon is centered about the valve and held in place for dilatation even though the heart continues to move. Referring to FIG. 14e, the middle portion of the balloon is inflated and the aortic valve is dilated. After dilatation of the valve, the balloon is deflated to a small profile and removed from the body.

In still other embodiments, the resistance to inflation provided by the constraint may be controlled by providing circumferential ribs or grooves along the sleeve, with fewer ribs provided at the distal portion, compared to the proximal portion, and still fewer ribs in the middle portion. In other embodiments, the sleeve may include circumferential slits. In other embodiments, the system may be provided with a stent positioned over the constraint and which is expanded by sequentially expanding the distal, proximal, and middle portions. The constraint can be constructed to permit expansion of portions in sequences other than those described above. For example, the constraint may permit a sequential inflation of only two balloon portions, e.g. distal followed by proximal. The systems can be adapted for use in other parts of the body, particularly where rapid, blind positioning and dilatation is desirable, such as in the gastrointestinal tract.

Other embodiments are within the following claims.

What is claimed is:

1. A medical system, comprising:
   a catheter having an inflatable balloon;
   a nonelastic constraint surrounding a portion of the balloon; and
   an expandable prosthesis disposed over the constraint,
   wherein, while surrounding the portion of the balloon, the constraint prevents the portion of the balloon from inflating.

2. The system of claim 1, comprising a plurality of constraints, the prosthesis disposed over at least two of the constraints.

3. The system of claim 1, comprising two constraints having different resistance to inflation pressure.

4. The system of claim 1, comprising a plurality of constraints positioned on the balloon in a predetermined sequence according to their resistance to inflation pressure.

5. The system of claim 1, comprising a plurality of constraints positioned on the balloon progressively according to their resistance to inflation pressure.

6. The system of claim 1, comprising a plurality of constraints having different thickness.

7. The system of claim 1, comprising a plurality of constraints positioned on the balloon sequentially according to thickness.

8. The system of claim 1, comprising a plurality of constraints positioned on the balloon progressively according to their thickness.

9. The system of claim 1, comprising a plurality of constraints arranged contiguously.

10. The system of claim 1, comprising a plurality of constraints extending the full length of the balloon.

11. The system of claim 1, wherein the constraint is separable from the expandable prosthesis.

12. The system of claim 1, wherein the constraint comprises Teflon®.

13. A method, comprising:
   delivering a medical system into the body, the medical system comprising
      a catheter having an inflatable balloon,
      a nonelastic constraint surrounding a portion of the balloon, and
      an expandable prosthesis disposed over the constraint, wherein, while surrounding the portion of the balloon, the constraint prevents the portion of the balloon from inflating; and
   inflating the balloon.

14. The method of claim 13 further comprising withdrawing from the body, the catheter and the constraint.

15. The method of claim 13, further comprising axially moving the constraint during inflation of the balloon.

16. A medical system, comprising:
a catheter having an inflatable balloon;
first and second nonelastic constraints surrounding portions of the balloon and constraining the portion of the balloon against inflation; and
an expandable prosthesis disposed over the constraints,
wherein the constraints have different resistance to inflation pressure.

17. A medical system, comprising:
a catheter having an inflatable balloon;
a plurality of nonelastic constraints surrounding portions of the balloon and constraining the portion of the balloon against inflation; and
an expandable prosthesis disposed over the constraints,
wherein the plurality of constraints are positioned on the balloon in a predetermined sequence according to their resistance to inflation pressure.

18. A medical system, comprising:
a catheter having an inflatable balloon;
a plurality of constraints surrounding portions of the balloon and constraining the portion of the balloon against inflation; and
an expandable prosthesis disposed over the constraints,
wherein the plurality of constraints are positioned on the balloon progressively according to their resistance to inflation pressure.

19. A medical system, comprising:
a catheter having an inflatable balloon;
a plurality of nonelastic constraints surrounding portions of the balloon and constraining the portion of the balloon against inflation; and
an expandable prosthesis disposed over the constraints,
wherein the plurality of constraints have different thickness.

20. A medical system, comprising:
a catheter having an inflatable balloon;
a plurality of nonelastic constraints surrounding portions of the balloon and constraining the portion of the balloon against inflation; and
an expandable prosthesis disposed over the contraints,
wherein the plurality of constraints are positioned on the balloon sequentially according to thickness.

21. A medical system, comprising:
a catheter having an inflatable balloon;
a plurality of constraints surrounding portions of the balloon and constraining the portion of the balloon against inflation; and
an expandable prosthesis disposed over the constraints,
wherein the plurality of constraints are positioned on the balloon progressively according to their thickness.

22. A medical system, comprising:
a catheter having an inflatable balloon;
a plurality of nonelastic constraints surrounding portions of the balloon and constraining the portion of the balloon against inflation; and
an expandable prosthesis disposed over the constraints,
wherein the plurality of constraints are arranged contiguously.

23. A medical system, comprising:
a catheter having an inflatable balloon;
a plurality of nonelastic constraints surrounding portions of the balloon and constraining the portion of the balloon against inflation; and
an expandable prosthesis disposed over the constraint,
wherein the plurality of constraints extend the full length of the balloon.

24. A medical system, comprising:
a catheter having an inflatable balloon;
a constraint surrounding a portion of the balloon; and
an expandable prosthesis disposed over the constraint,
wherein, while surrounding the portion of the balloon, the constraint prevents the portion of the balloon from inflating, and wherein the constraint is configured to move axially during inflation of the balloon.

* * * * *